(12) United States Patent
Sasaki

(10) Patent No.: US 9,573,919 B2
(45) Date of Patent: Feb. 21, 2017

(54) PEROXISOME PROLIFERATOR-ACTIVATED RECEPTOR (PPAR) ACTIVATOR, AND DRUGS, SUPPLEMENTS, FUNCTIONAL FOODS AND FOOD ADDITIVES USING THE SAME

(75) Inventor: Takao Sasaki, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 1113 days.

(21) Appl. No.: 11/800,637

(22) Filed: May 7, 2007

(65) Prior Publication Data

US 2007/0213282 A1    Sep. 13, 2007

Related U.S. Application Data

(63) Continuation-in-part of application No. PCT/JP2005/020268, filed on Nov. 4, 2005.

(30) Foreign Application Priority Data

Nov. 8, 2004 (JP) ................................. 2004-324015

(51) Int. Cl.
*C07D 311/30*     (2006.01)
*A61K 31/352*    (2006.01)
*A61K 36/752*    (2006.01)

(52) U.S. Cl.
CPC .......... *C07D 311/30* (2013.01); *A61K 31/352* (2013.01); *A61K 36/752* (2013.01)

(58) Field of Classification Search
None
See application file for complete search history.

(56) References Cited

U.S. PATENT DOCUMENTS

| 6,303,586 B1 * | 10/2001 | McPeak et al. ................ 514/54 |
| 2002/0040052 A1 * | 4/2002 | Ito et al. ..................... 514/456 |
| 2006/0199761 A1 | 9/2006 | Kadowaki et al. |

FOREIGN PATENT DOCUMENTS

| JP | 2000-247880 | 9/2000 |
| JP | 2000-247880 A | 9/2000 |
| JP | 2001-240539 | 9/2001 |
| JP | 2001-240539 A | 9/2001 |
| JP | 2002-080362 | 3/2002 |
| JP | 2002-080362 A | 3/2002 |
| JP | 2000-80035 | 3/2003 |
| JP | 2004-137218 | 5/2004 |
| WO | 02/055071 | 7/2002 |
| WO | 02/087567 | 11/2002 |
| WO | 03/063894 A1 | 8/2003 |

OTHER PUBLICATIONS 2010 http://www.diabetes.org/diabetes-basics/genetics-of-diabetes.html.*
translation of JP 20011240539.*
Ito et al. translation.*
Kurowska, et al., "Modulation of HepG2 Cell Net Apolipoprotein B Secretion by the Citrus Polymethoxyflavone, Tangeretin", Lipids, vol. 39, No. 2 (2004), pp. 143-151.
Lim, et al., "15-Deoxy-$\Delta^{12, 14}$-Prostaglandin $J_2$ Protects against Nitrosative PC12 Cell Death through Up-regulation of Interacellular Glutathione Synthesis", The Journal of Biological Chemistry, vol. 279, No. 44, Oct. 29, 2004, pp. 46263-46270.
Fuenzalida, et al., "Peroxisome Proliferator-activated Receptor γ Is a Novel Target of the Nerve Growth Factor Signaling Pathway in PC 12 Cells", The Journal of Biological Chemistry, vol. 280, No. 10, Mar. 11, 2005, pp. 9604-9609.
Eguchi et al., "Suppressive effects of food factors on the expression of lectin-like oxidized LDL receptor-1 (LOX-1)," Annual Meeting Brochure of Japanese Society for Bioscience, Biotechnology, and Agrochemistry, 2A16p11, p. 61, (2004).
Office Action issued in corresponding Japanese Patent Application No. 2013-101529 dated Jun. 3, 2014.
Yamauchi et al., "The fat-derived hormone adiponectin reverses insulin resistance associated with both lipoatrophy and obesity," Nature Medicine, 7: 941-946 (2001).

* cited by examiner

*Primary Examiner* — Terry A McKelvey
*Assistant Examiner* — Catheryne Chen
(74) *Attorney, Agent, or Firm* — Morgan, Lewis & Bockius LLP

(57) ABSTRACT

The present invention provides a peroxisome proliferator-activated receptor (PPAR) activator, which is free from the problem of side effects, can be taken over a long term and has no characteristics taste. Nobiletin is employed as a PPAR activator. Nobiletin has an excellent PPAR activity and has an excellent adiponectin secretion-promoting effect, and is contained in a large amount in *citrus* fruits, in particular, in Shiikuwasha (*Citrus depressa* HAYATA) indigenous to Okinawa (Japan). Since *citrus* fruits have been consumed for many years, the safety of nobiletin has been proven and besides, nobiletin has a low calorie content. Therefore, it can be taken over a long term. Moreover, because of being tasteless and odorless, nobiletin would not damage the unique taste of a food when added thereto. Therefore, it can be added to foods and taken.

10 Claims, 2 Drawing Sheets

PEROXISOME PROLIFERATOR-ACTIVATED RECEPTOR (PPAR) ACTIVATOR, AND DRUGS, SUPPLEMENTS, FUNCTIONAL FOODS AND FOOD ADDITIVES USING THE SAME

TECHNICAL FIELD

The present invention relates to a peroxisome proliferator-activated receptor (PPAR) activator, and drugs, supplements, functional foods and food additives using the same.

BACKGROUND ART

The development of diabetes is said to be associated with two factors, namely, a decrease in insulin secretion and an insulin resistance. Recently, a greater number of Japanese people have become afflicted with diabetes. Since the decrease in insulin secretion mostly is attributable to genetic factors, it is considered that a major cause of the increase in the number of diabetics is not the decrease in insulin secretion but the insulin resistance. Such an insulin resistance reportedly is caused by an increase in fat intake due to westernized dietary habits of Japanese people as well as lack of exercise, obesity and stress. Recent studies have revealed that the mechanism of the occurrence of insulin resistance is ascribable to hypertrophic adipocytes. In other words, hypertrophic adipocytes cause TNF-α and free fatty acid (FFA) to be secreted, thus not only impairing the sugar intake in muscle cells and liver cells but also inhibiting the secretion of adiponectin, which promotes a function of insulin, so that the insulin resistance occurs.

On the other hand, studies of the insulin resistance have shown that the activation of PPARs, which are intranuclear receptors, is effective in relieving the insulin resistance. PPARs are known to have three types, i.e., α, σ and γ, and several subtypes. PPARα is expressed mainly in the liver cells and also in other cells such as myocardial cells and gastrointestinal cells, and associated with fatty acid oxidation, ketogenesis and apolipoprotein generation. Although PPARσ is not considered to have tissue specificity and is expressed throughout the body, it is expressed notably in colon cancer cells. PPARγ can be classified into two subtypes, i.e., type γ1 and type γ2. The type γ1 is expressed in adipose tissues, immune system tissues, the adrenal gland and the small intestine, whereas the type γ2 is expressed specifically to adipocytes and plays an important role in differentiation induction of the adipocytes and fat synthesis.

As described above, PPARs greatly are involved with the relief of insulin resistance. In addition, PPARs are said to be associated with the relief of hyperinsulinism, type II diabetes as well as obesity, hypertension, hyperlipemia and arteriosclerosis. From this viewpoint, studies have been conducted on substances that activate PPARs, and synthetic substance-based PPAR activators such as fibrate compound, thiazolidine derivatives, fatty acids, leukotriene B4, indomethacin, ibuprofen, fenoprofen, and 15-deoxy-Δ-12,14-PGJ2 are known, for example. However, since such synthetic substance-based PPAR activators have a problem of side effects caused by long-term intake, they are not suitable for preventing or relieving diseases such as the insulin resistance by daily intake. Other than the above, natural substances such as curcumin contained in turmeric, monoacylglycerol, which is one kind of fats and oils, catechins contained in tea, etc. have been reported as PPAR activators derived from natural components (see Patent document 1, for example). However, fats and oils have a high calorie content, though they are derived from natural components, and therefore, a problem arises if they are taken continuously. Further, although it is ideal that the natural component-derived PPAR activators be added to foods or the like for daily intake, they are not suitable for the addition to foods or the like because they often have peculiar tastes.

Patent document 1: JP 2002-80362 A

DISCLOSURE OF INVENTION

Problem to be Solved by the Invention

The present invention was made with the foregoing in mind, and it is an object of the present invention to provide a PPAR activator that is free from a problem of side effects, can be taken for a long term and does not cause any problem even when added to foods or the like.

Means for Solving Problem

In order to achieve the above-mentioned object, a PPAR activator according to the present invention contains nobiletin.

Effects of the Invention

For the purpose of solving the problems described above, the inventor of the present invention conducted a series of studies on PPAR activators of natural components and found that nobiletin, which was contained in *citrus* fruits, in particular, in Shiikuwasha (the academic name: *Citrus depressa* HAYATA) indigenous to Okinawa (Japan), had a PPAR activating function, thus arriving at the present invention. In other words, Shiikuwasha containing a large amount of nobiletin has been eaten for many years and confirmed in terms of safety. Also, nobiletin has a low calorie content and, in this regard, does not cause any problem even if it is taken by a diabetic, an obese patient or the like for a long term. Further, since nobiletin is tasteless and odorless, it does not impair the unique taste of a food or the like when added to this food, so that it can be added to foods and taken daily over a long term. Therefore, in accordance with the present invention, nobiletin activates PPARs, thereby promoting fat burning, thus inhibiting the secretion of TNF-α and free fatty acid and promoting the secretion of adiponectin. Accordingly, it is possible to normalize the state of adipocytes and relieve the insulin resistance and other symptoms such as hyperinsulinism, type II diabetes, hypertension, hyperlipemia, arteriosclerosis and obesity. It should be noted that this is effective for not only humans but also other animals.

DESCRIPTION OF THE INVENTION

Figure 1:
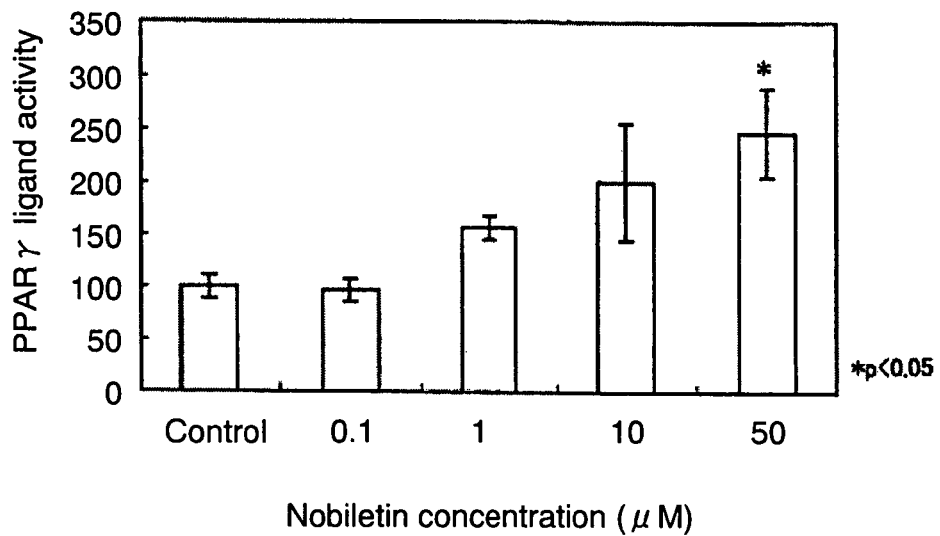
FIG. 1 is a graph showing a PPARγ ligand activity of nobiletin in an example of the present invention.

In a PPAR activator according to the present invention, the PPAR to be activated may be either PPARα or PPARγ, for example, and preferably is both of them. The PPAR activator of the present invention may contain components other than nobiletin. Examples of the components other than nobiletin include various additives and PPAR activators other than nobiletin.

As described above, since nobiletin has a PPAR activating function, the PPAR activator according to the present invention exhibits, in adipocytes, a function of inhibiting the secretion of TNF-α and free fatty acid or a function of promoting the secretion of adiponectin, and exhibits, in liver cells, promoting β oxidation of fat, for example. Moreover, the PPAR activator according to the present invention induces at least one of apoptosis, differentiation, and shrinkage of an adipocyte, for example.

In the PPAR activator according to the present invention, the nobiletin to be used is not particularly limited, and examples thereof include those derived from *citrus* fruits, preferably from Shiikuwasha known as a fruit indigenous to Okinawa. The fruit juice of Shiikuwasha contains a large amount of nobiletin and thus can be used as it is. Alternatively, nobiletin may be obtained by isolation and purification from a *citrus* fruit or may be a commercially available product, for example.

Next, a drug according to the present invention is a drug for preventing or treating at least one disease selected from the group consisting of insulin resistance, hyperinsulinism, type II diabetes, hypertension, hyperlipemia, arteriosclerosis and obesity, for example, and the drug contains the PPAR activator according to the present invention. The drug of the present invention may contain not only the PPAR activator according to the present invention but also other PPAR activators and various additives, for example. In the drug according to the present invention, examples of its specific dosage form can include tablets, granules (including powder), capsules, solutions (including a syrup) and the like. The drug according to the present invention can be prepared by using an additive or a base, etc. that is suitable for each dosage form as appropriate according to a regular method described in the Pharmacopoeia of Japan or the like. Also, a route of administration is not particularly limited but can be, for example, an oral administration or a parenteral administration. Examples of the parenteral administration can include intraoral administration, tracheobronchial administration, intrarectal administration, subcutaneous administration, intramuscular administration, intravenous administration and the like. In the drug according to the present invention, the content of nobiletin may be such that the daily dose of nobiletin is at least 10 mg, preferably at least 20 mg, for example.

Now, a supplement according to the present invention is a supplement for preventing or relieving at least one disease selected from the group consisting of insulin resistance, hyperinsulinism, type II diabetes, hypertension, hyperlipemia, arteriosclerosis and obesity, and the supplement contains the PPAR activator according to the present invention. The supplement of the present invention may contain not only the PPAR activator according to the present invention but also other PPAR activators, various additives, other supplements and the like, for example. Examples of the above-noted other supplements can include various vitamins such as vitamin C, amino acids and oligosaccharides. The supplement according to the present invention may be in any form without particular limitation, which can be, for example, tablets, granules (including powder), capsules, solution (including syrup) or the like. In the supplement according to the present invention, the content of nobiletin may be the same as that described in the above with regard to the drug.

Next, a functional food according to the present invention is a functional food for preventing or relieving at least one disease selected from the group consisting of insulin resistance, hyperinsulinism, type II diabetes, hypertension, hyperlipemia, arteriosclerosis and obesity, and the functional food contains the PPAR activator according to the present invention. The functional food of the present invention may contain not only the PPAR activator according to the present invention but also other PPAR activators, various additives and the like, for example. Note here that the functional food according to the present invention may be in any form without particular limitation, which can be, for example, noodles, confectionery, functional drinks or the like.

Now, a food additive according to the present invention is a food additive for preventing or relieving at least one disease selected from the group consisting of insulin resistance, hyperinsulinism, type II diabetes, hypertension, hyperlipemia, arteriosclerosis and obesity, and the food additive contains the PPAR activator according to the present invention. The food additive of the present invention may contain not only the PPAR activator according to the present invention but also other PPAR activators, various additives and the like, for example. The food additive according to the present invention may be in any form without particular limitation, which can be, for example, liquid, paste, powder, flakes, granule or the like. Moreover, the food additive according to the present invention includes food additives for drinks.

Next, a method for activating a PPAR according to the present invention is a method for activating a PPAR by nobiletin. Preferably, the PPAR is activated by bringing nobiletin into contact with adipocytes or the like, for example.

In the method for activating a PPAR according to the present invention, the nobiletin to be used is the same as that used for the above-noted PPAR activator according to the present invention, and examples thereof include those derived from *citrus* fruits, preferably from Shiikuwasha known as a fruit indigenous to Okinawa. Since the fruit juice of Shiikuwasha contains a large amount of nobiletin as described above, it can be used as it is. Alternatively, nobiletin may be obtained by isolation and purification from a *citrus* fruit or may be a commercially available product, for example.

Now, a method for preventing, treating or relieving a disease according to the present invention is a method for preventing, treating or relieving at least one disease selected from the group consisting of insulin resistance, hyperinsulinism, type II diabetes, hypertension, hyperlipemia, arteriosclerosis and obesity in a mammal, and the method includes administering nobiletin. The daily dose of nobiletin may be at least 10 mg, preferably at least 20 mg, for example. The above-noted mammal can be, for example, a human, a mouse, a rat, a rabbit, a dog, a cat, a cow, a horse, a swine, a monkey or the like.

Next, a kit according to the present invention is a kit for preventing or treating at least one disease selected from the group consisting of insulin resistance, hyperinsulinism, type II diabetes, hypertension, hyperlipemia, arteriosclerosis and obesity, and the kit includes:
a) nobiletin;
b) a second drug composition containing a second compound useful for preventing or treating at least one disease selected from the group consisting of insulin resistance, hyperinsulinism, type II diabetes, hypertension, hyperlipemia, arteriosclerosis and obesity; and c) a container for containing the nobiletin and the second drug composition.

Now, use according to the present invention is use of nobiletin for preparing a PPAR activator.

Further, use according to the present invention is use including administering nobiletin for preventing, treating or relieving at least one disease selected from the group consisting of insulin resistance, hyperinsulinism, type II diabetes, hypertension, hyperlipemia, arteriosclerosis and obesity in a mammal. The daily dose of nobiletin and the mammal are as described above.

In the use according to the present invention, the nobiletin to be used is the same as that usable for the above-noted PPAR activator according to the present invention, and examples thereof include those derived from *citrus* fruits, preferably from Shiikuwasha known as a fruit indigenous to Okinawa. In particular, *citrus* fruits are preferable. Since the fruit juice of Shiikuwasha contains a large amount of nobiletin as described above, it can be used as it is. Alternatively, nobiletin may be obtained by isolation and purification from a *citrus* fruit or may be a commercially available product, for example.

In the use according to the present invention, the nobiletin induces at least one of the functions of inhibiting the secretion of TNF-α and free fatty acid in adipocytes, promoting the secretion of adiponectin in adipocytes and promoting β oxidation of fat in liver cells, for example. Moreover, in the use according to the present invention, the nobiletin induces at least one of apoptosis, differentiation, shrinkage and the like of an adipocyte, for example.

Nobiletin used in the present invention can be produced from a *citrus* fruit such as Shiikuwasha in the following manner, for example.

First, the fruit is cut or crushed to a desired size. The fruit to be used may be in a fresh state immediately after being harvested or in a dried state. Next, pieces of the fruit obtained by cutting or the like are immersed in a solvent to obtain an extract. Examples of the solvent used for immersion include: water; lower alcohols such as methanol, ethanol, n-propanol, isopropanol, and t-butanol; ketones such as acetone; ethers such as diethyl ether and petroleum ether; chlorine-based organic solvents such as chloroform and dichloromethane. They may be used alone or in combination of at least two kinds thereof. Among these, it is preferable to use a mixture of water and ethanol or ethanol in terms of toxicity or the like. The amount of the solvent to be used is not particularly limited, and can be in the range from 200 to 10000 parts by weight with respect to 100 parts by weight of the fruit, for example. The extracting treatment can be performed, for example, at room temperature, preferably at a temperature in the range from 4° C. to 120° C., more preferably at a temperature in the range from 40° C. to 100° C. The extracting time can be determined as appropriate depending on the extracting temperature etc. For example, the extracting time is 1 to 10 days at room temperature, and 1 to 96 hours at 50° C. or higher.

Subsequently, the extract is separated and taken out from the residual substance through filtration using a filter, or the like. The thus-obtained extract or a dried product thereof contains nobiletin and hence, they can be used as they are. Moreover, as will be described later, they may be used after being purified so as to improve the purity of nobiletin.

The purification of the extract can be achieved by, for example, silica gel chromatography using a suitable eluent. As the eluent, it is preferable to use, for example, a mixed solvent of a solvent such as ethyl acetate, methanol, isopropyl ether, tetrahydrofuran, benzene or xylene and a solvent such as hexane, heptane, chloroform, or dichloroethane.

Example 1

As described in the following, the present example verified the activation of PPARγ by nobiletin.

First, CV-1 cells (cultured cells derived from kidneys of male African green monkeys) were inoculated on 24-well culture plates so as to be 0.2 µg/well and cultured at 37° C. in 5% $CO_2$ for 24 hours. As a medium, DMEM (Dulbecco's Modified Eagle Medium; available from GIBCO) containing 10% FBS (fetal bovine serum) and a 10 mg/ml penicillin streptomycin solution was used. Next, using the Lipofectamine system (Invitrogen Corporation), pM-hPPARγ and p4×UASg-tk-luc were transfected into the cultured CV-1 cells. The above-noted pM-hPPARγ was a vector for expressing fusion protein containing residues 1-147 of GAL4 binding domain and residues 204-505 of human PPARγ ligand-binding domain, and the above-noted p4×UASg-tk-luc was a reporter plasmid containing four copies of an upstream activating sequence (UAS) for GAL4 binding domain and a thymidine kinase gene promoter upstream of a luciferase gene. After the transfection, the cells were cultured for about 24 hours, and then, the media for the cells were changed to media containing nobiletin at respective concentrations (0.1, 1.0, and 50 µM) or media for non-treatment control, followed by an additional 24 hour culture. The above-noted media containing nobiletin were prepared by adding nobiletin dissolved in dimethyl sulfoxide (DMSO) to the media, whereas the media for non-treatment control were prepared by adding only DMSO to the media. After the culture, the cells were lysed and the measurement of luciferase activity was performed using a Dual-Luciferase Reporter Gene Assay system (available from Promega Corporation) (Measurement Group).

Similarly to the measurement group, as a control group, the measurement of luciferase activity was performed using pM (a vector containing residues 1-147 of GAL4 binding domain and not containing residues 204-505 of PPARγ ligand-binding domain in pM-hPPARγ) instead of the pM-hPPARγ. For each sample, the ratio between average luminescence intensities of the measurement group and the control group (n=4) (measurement group/control group) was calculated, and the luciferase activity relative to the non-treatment control was determined as the PPARγ ligand-binding activity of the sample. Table 1 below and the graph of FIG. 1 show the results.

TABLE 1

|  | Addition concentration | PPARγ ligand activity |
|---|---|---|
| Non-treatment control (DMSO) | (0.1%) | 100 |
| nobiletin | 0.1 µM | 96.5 ± 10.8 |
|  | 1.0 µM | 156.8 ± 11.3 |
|  | 10 µM | 200.5 ± 55.1 |
|  | 50 µM | 246 ± 41.7 |
|  |  | (average ± standard error) |

As becomes clear from Table 1 and FIG. 1 mentioned above, the nobiletin improved the PPARγ activity such that the PPARγ activity increased significantly in keeping with the concentration of nobiletin.

Example 2

As described in the following, the present example verified the adiponectin secretion-promoting effect of nobiletin.
(Differentiation Induction of Preadipocyte)
First, the following two kinds of media were prepared.
1. Differentiation Induction Medium (0.25 μM DEX, 0.5 mM MIX, 10 μg/Ml insulin/10% FBS/DMEM)
55 ml of FBS (fetal bovine serum (available from GIBCO)) was added to 500 ml of DMEM (available from SIGMA) so as to prepare 10% FBS/DMEM. To this 10% FBS/DMEM, 138.75 μl of 1 mM DEX (dexamethasone)/DMSO (available from Nacalai Tesque, Inc.) and 555 μl of 10 mg/ml insulin/PBS (available from SIGMA) were added. Note here that the insulin/PBS was obtained by adding 1 N HCl to PBS in advance so as to make the solution acidic enough to allow insulin dissolution and then dissolving insulin. MIX (3-isobutyl-1-methylxanthine) (available from Nacalai Tesque, Inc.) was added to a necessary amount of the above-described medium immediately before use in such a manner as to achieve 0.5 mM concentration, thereby preparing a differentiation induction medium. Since MIX was very difficult to dissolve, it first was dissolved in a small amount of 99.5% ethanol and then added to 10% FBS/DMEM. At this time, an adjustment was made so that the final concentration of 99.5% ethanol did not exceed 1%.
2. Differentiation Promotion Medium (5 μg/Ml Insulin/10% FBS/DMEM)
A differentiation promotion medium was prepared by adding 277.5 μl of 10 mg/ml insulin/PBS to 555 ml of 10% FBS/DMEM.

Next, cultured preadipocytes 3T3-L1 were thawed, inoculated in a 100 mm dish and cultured until the 3T3-L1 cells reached about 80% confluence. A single dish of 3T3-L1 that had reached about 80% confluence was subcultured to a single 6-well plate and further cultured until the 3T3-L1 cells reached confluence in the 6-well plate, and then the medium was replaced with the differentiation induction medium, followed by differentiation induction. 48 hours later, the medium was replaced with the differentiation promotion medium, and thereafter, the medium was replaced with the differentiation promotion medium every two days. 7 days after the initiation of the differentiation induction, mRNA was extracted using a Sepasol-RNA I Super (trade name; available from Nacalai Tesque, Inc.), and the mRNA expression amounts of 36B4, aP2 and adiponectin, which were indicators of an early period of adipocyte differentiation, were measured using a Light Cycler™.
(Quantification of mRNA using Light Cycler™)
Extraction and Quantification of Total RNA
The medium was removed from the above-described Swell plate, 1 ml of Sepasol-RNA I Super (available from Nacalai Tesque, Inc.) was added to each well, and pipetting was repeated several times so as to disperse the cells. This solution was transferred to a 1.5 ml tube and allowed to stand for 5 minutes at room temperature, and then 200 μl of chloroform was added, stirred well with a vortex and allowed to stand for 3 minutes at room temperature. The solution was cooled to 4° C. and centrifuged at 12000×g for 15 minutes. While taking care not to disturb an interface between a phenol layer (a lower layer, yellow) and a water layer (an upper layer, colorless), the water layer alone was transferred to another tube (with a capacity of 1.5 ml). At this time, care was taken not to take proteins floating between these layers. 500 μl of isopropanol was added to the tube and mixed and allowed to stand for 10 minutes at room temperature. The solution was cooled to 4° C. and centrifuged at 12000×g for 10 minutes, followed by removing about 1 ml of the supernatant. To this precipitate, 1 ml of 75% ethanol was added and stirred to suspend the precipitate sufficiently, and then cooled to 4° C. and centrifuged at 12000×g for 10 minutes, followed by removing the supernatant. The resultant precipitate (total RNA) was dried and then dissolved in 20 μl of nuclease free water, and the concentration of mRNA was measured using Nanoprop (available from SCRUM Inc.).

Reverse Transcription

The extracted and measured mRNA solution was adjusted to have an mRNA concentration of 1 μg/μl. 1 μl of Oligo dT primer and 10 μl of the above-described RNA solution were added to 8-tube strips (with a capacity of 0.2 ml). The mixture solution was incubated in a thermal cycler at 70° C. for 10 minutes so as to destroy higher-order structures of RNA, and transferred onto the ice and allowed to stand for at least 1 minute. Then, reagents shown below were added one after another.

TABLE 2

| RNA sample/primer mixture solution | 11 μl |
| 5× reverse transcription buffer | 5 μl |
| RNase inhibitor | 1 μl |
| 2.5 mM dNTP Mix | 5 μl |
| Nuclease free water | 2 μl |
| Total | 24 μl |

After pre-incubation at 42° C. for 5 minutes in a thermal cycler, 1 μl of reverse transcriptase was added, and the content of the tube was mixed well by pipetting. After incubation at 42° C. for 50 minutes and further incubation at 70° C. for 15 minutes in a thermal cycler, the content was cooled on ice and centrifuged mildly so as to collect the reaction solution to the tube bottom, and then cryopreserved at −20° C. Every time it was used for the Light Cycler™ measurement, it was diluted by 10 times.

Measurement using Light Cycler™

All the operations described below were carried out in a clean bench. 5 μl of a plasmid solution containing fragments of the gene whose expression amount was to be measured was poured in a 0.65 ml tube and diluted by 10 times with 45 μl of water attached to a Light Cycler™ DNA Master SYBR Green (trade name). By repeating these operations, $10^2$-time, $10^3$-time, $10^4$-time, $10^5$-time, $10^6$-time, $10^7$-time and $10^8$-time diluted solutions were produced, respectively. A dedicated capillary tube was set into a Light Cycler™ Centrifuge Adapter (trade name) using tweezers, and 18 μl each of the above-noted reagents were dispensed thereto. Further, 2 μl of water as a negative control, the seven levels of diluted solutions as standards, and 2 μl of 10-time diluted solution of cDNA of a measurement sample were added, and a lid was placed using tweezers. After centrifugation at 5000 rpm at 4° C. for 10 seconds, the capillary tubes were inserted into a carousel, which then was set in a chamber and subjected to measurement.

Figure 2:
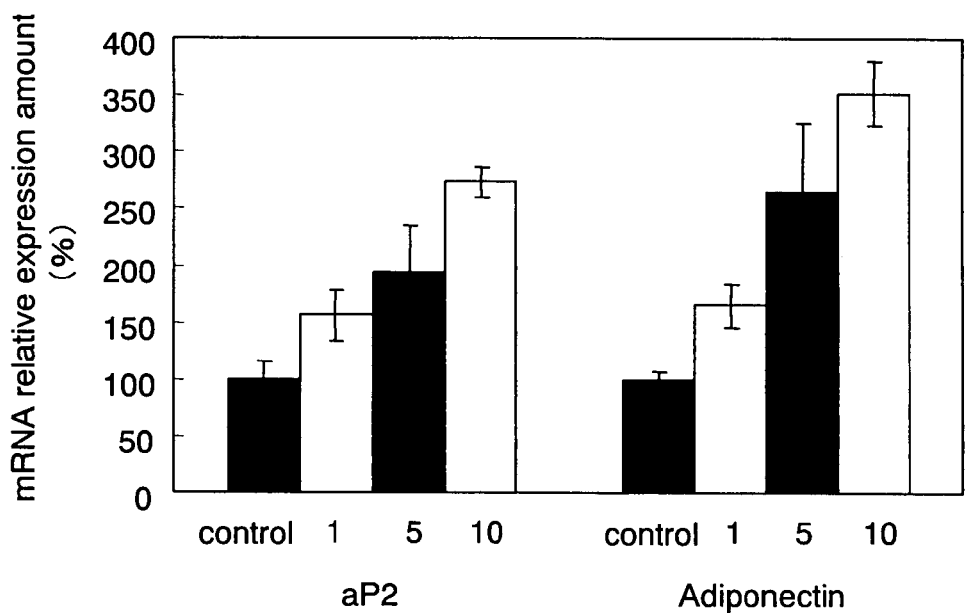
FIG. 2 is a graph showing an increase in adiponectin mRNA expression amount by nobiletin in another example of the present invention.

Using the results of quantification with the Light Cycler™, the ratio of the respective mRNA expression amounts of aP2 and adiponectin with respect to the mRNA expression amount of 36B4 was calculated for each sample. The results of the calculation are shown in Table 3 below and the graph in FIG. 2.

TABLE 3

| | Addition concentration | aP2 | Adiponectin |
|---|---|---|---|
| Non-treatment control | | 100 ± 16.2 | 100 ± 6.9 |
| Nobiletin | 1 μm | 155.8 ± 21.7 | 164.9 ± 18.7 |
| | 5 μM | 193.7 ± 41.4 | 265.1 ± 60.4 |
| | 10 μM | 273.1 ± 13.8 | 352.3 ± 28.5 |
| | | | (average ± standard error) |

When adipocytes cultured in the differentiation induction media to which nobiletin was added and adipocytes cultured in the non-treated control medium were compared, the addition of nobiletin was found to enhance the secretion of adiponectin in the adipocytes significantly. This demonstrates that nobiletin has an effect of promoting adiponectin secretion.

Example 3

The present example verified the diabetes relieving-effect of nobiletin through an experiment using spontaneously diabetic mice (KK-A$^y$).

First, twelve spontaneously diabetic mice (6-week old, female) were fed preliminarily with normal diet for one week. Next, the mice were divided into two groups, namely, a control group and a NOB group (n=6) such that the average weights of these two groups were the same. Then, the mice of the control group were fed with high-fat diet only, whereas the mice of the NOB group were fed with high-fat diet containing 0.02% nobiletin. 27 days or 28 days after the initiation of feeding, serum was collected from these mice. Note here that nobiletin derived from an extract of Shiikuwasha was used in the present example.

(Measurement of Adiponectin Secretion Amount Using ELISA)

Measurement of the adiponectin secretion amount using an enzyme linked immunosorbent assay (ELISA) was performed with the use of a mouse/rat adiponectin ELISA kit (Otsuka Pharmaceutical Co., Ltd.). The kit had the following configuration.
Stock solution for washing
Stock solution for diluting specimen
Antibody plate (anti-mouse adiponectin polyclonal antibody (rabbit) solid phase plate)
8.0 ng/ml reference standard (recombinant mouse adiponectin)
Biotin-labeled antibody solution (biotin-labeled anti-mouse adiponectin polyclonal antibody (rabbit))
Enzyme-labeled streptavidin stock solution (HRP-labeled streptavidin)
Enzyme-labeled streptavidin diluent
Substrate solution A (3,3',5,5'-tetramethylbenzidine)
Substrate solution B (hydrogen peroxide)
Reaction stop solution
First, the following reagents and specimen solution were prepared.
Washing Solution
The above-noted stock solution for washing and purified water were mixed in a ratio of 40 ml to 960 ml and stored at 2.8° C.
Specimen Diluent
The above-noted stock solution for diluting specimen and purified water were mixed in a ratio of 50 ml to 200 ml and stored at 2.8° C.
Standard Solution
The above-noted 8.0 ng/ml reference standard was diluted with the above-described specimen diluent two times gradually so as to prepare standard solutions having a concentration of 4.0 ng/ml, 2.0 ng/ml, 1.0 ng/ml, 0.5 ng/ml and 0.25 ng/ml.
Enzyme-Labeled Streptavidin Solution
The above-noted enzyme-labeled streptavidin diluent and the above-noted enzyme-labeled streptavidin stock solution were mixed in a ratio of 12 ml to 60 μl.
Substrate Solution
The above-noted substrate solution B and the above-noted substrate solution A were mixed in a ratio of 6 ml to 6 ml.
Specimen Solution
The serums collected from the mice of the control group and NOB group were diluted by 40,000 times.

Figure 3:
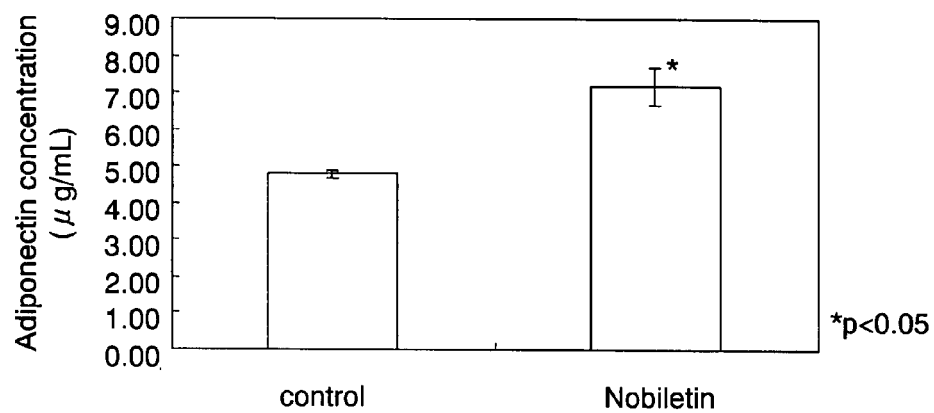
FIG. 3 is a graph showing a diabetes-relieving effect by nobiletin in yet another example of the present invention.

Only the strips of the antibody plates necessary for the analysis were taken out. After about 200 μl of the above-described washing solution was poured to each well of the antibody plate, the liquid in the well was absorbed and removed completely using a plate washer. This washing and absorption were performed once more. Thereafter, 100 μl of the standard solutions with respective concentrations and 100 μl of the diluted specimen solutions were added to the individual wells and measured in duplicate. Note here that the standard solutions always were measured for each measurement and each plate. After the antibody plate was covered with a plate seal and allowed to stand still for reaction for 60 minutes at room temperature, the plate seal was removed from the antibody plate, followed by absorbing and removing completely the liquid in the wells using the plate washer. Subsequently, about 200 μl of the washing solution was added to each well and immediately was absorbed and removed. This washing and absorption were repeated four more times. After 100 μl of the biotin labeled antibody solution was added to each well of the antibody plate, the antibody plate was covered with a plate seal and allowed to stand still for reaction for 60 minutes at room temperature. Similarly to the above, the washing of the wells and absorption were repeated to a total of five times. After 100 μl of the enzyme-labeled streptavidin solution was added to each well of the antibody plate, the antibody plate was covered with a plate seal and allowed to stand still for reaction for 60 minutes at room temperature. Similarly to the above, the washing of the wells and absorption were repeated to a total of five times. After 100 μl of the substrate solution was added to each well of the antibody plate and allowed to stand still for reaction for 15 minutes at room temperature, 100 μl of the reaction stop solution was added to each well of the antibody plate, and then the absorbance at 450 nm in each well was measured with a plate reader. The results (the average values) of the adiponectin secretion amount measurement, which were obtained through the above-described absorbance measurement, are shown in Table 4 below and the graph in FIG. 3.

TABLE 4

| | Nobiletin content | Adiponectin secretion amount |
|---|---|---|
| Control group | 0% | 4.78 ± 0.096 |
| NOB group | 0.02% | 7.18 ± 0.50 |
| | | (average ± standard error) |

As a result of the comparison of adiponectin secretion amount between the diabetic mice of the NOB group with the intake of nobiletin and the diabetic mice of the control group without the intake of nobiletin, the intake of nobiletin was found to increase the adiponectin secretion amount in the adipocytes significantly. This result suggests that when diabetics take nobiletin, adiponectin secretion is promoted to normalize the state of adipocytes, thereby relieving diabetes. Thus, it can be said that nobiletin has an effect of relieving diabetes.

Example 4

The present example verified the adiponectin secretion-promoting effect of nobiletin in humans.

(Test Food•Placebo Food)

A test food in the form of a capsule-shaped food product was prepared using a Shiikuwasha extract, dextrin, gelatin (derived from swine), starch, stearic acid Ca, caramel pigment, titanium dioxide, and lecithin (derived from soy beans) as raw materials. In this test food, the Shiikuwasha extract was contained in an amount of 667 mg per 5 capsules of the test food. A reference daily intake of the test food was set to 5 capsules. Nutrients contained in 5 capsules of the test food were 2.1 kcal of energy, 0.3 g of protein, 0.1 g of lipid, 1.0 g of carbohydrates, and 0.4 mg of sodium. In 5 capsules of the test food, a total content of nobiletin and tangeretin was 20 mg. The Shiikuwasha extract used was obtained by separation and purification from a residual substance (pericarp or the like) produced in a process for manufacturing concentrated fruit juice of Shiikuwasha The placebo food was obtained by replacing the Shekwasha extract in the test food with dextrin and was made so as not to be distinguishable from the test food by its color, shape, size, feeling on the tongue, flavor or the like. The placebo food was prepared using starch, dextrin, gelatin (derived from swine), caramel pigment, stearic acid Ca, titanium dioxide, and lecithin (derived from soy beans). Further, nutrients contained in 5 capsules of the placebo food were 6.6 kcal of energy, 0.3 g of protein, 0.0 g of lipid, 1.3 g of carbohydrates, and 3.5 mg of sodium.

(Test Subject)

A test was performed with respect to 33 Japanese adult males and females. Further, these people were selected based on the criterion of having a visceral fat area of 100 $cm^2$ or larger. By a person who is not involved directly in the test but is responsible for test food assignment, these 33 people were divided into two groups, i.e. a test food group of people taking the test food and a placebo food group of people taking the placebo food so as to be distributed evenly in the groups in terms of a visceral fat area, age and sex. Among these subjects, one ended up not participating in the test for a personal reason, and therefore, the definitive number of the subjects examined was 32. Incidentally, a medical doctor responsible for performing human tests confirmed that the one subject having been untested was not attributable to the taking of the test food or each examination performed in this test.

With the approval by the Human Test Ethics Committee in Japan, the present example was implemented in compliance with the spirit of the Helsinki Declaration (adopted on 1964, revised on 2000, and annotated on 2002) under the supervision of a medical doctor. Each of the subjects was informed of an implementation plan of the test, fully understood the contents thereof, wished to participate in the test on a voluntary basis, and participated in the test upon submission of a written consent.

(Test Method)

The test adopted the double-blind method and took the form of a placebo-controlled parallel intergroup comparison trial. Each of the subjects took the test food in an amount five times greater than the reference daily intake (5 capsules of the test food as described above) continuously for eight weeks. Physical examinations (a blood test, an urine test, body measurements, sphygmomanometry and medical diagnosis) were carried out three times in total, i.e. on the test food taking starting day, after four weeks of the food taking and after eight weeks of the food taking. Further, CT (Computed Tomography) on the umbilicus section in the transverse plane was carried out twice, i.e. on the food taking starting day and after eight weeks of the food taking. The subjects were instructed to avoid gluttony as well as excess exercise and to maintain their living habits during the test period. Also, a life logbook was distributed to each of the subjects, with which they made daily records of the test food taking condition, health condition, living conditions (food size, exercise volume, alcohol intake and the like). Further, on each of three days before the physical examinations were performed, a dietary log was kept and an exercise volume was measured using a pedometer.

(Statistical Analysis)

Each of measurement values as results of the quantification was represented by an average value±a standard deviation. Data compilation was performed using Microsoft Office Excel 2003 (Manufactured by Microsoft Corporation). Statistical analysis was performed using Dr. SPSS II for Windows (manufactured by SPSS Inc.), and an assay was performed at a hazard ratio of 5% (two-sided).

(Results)

Figure 4:
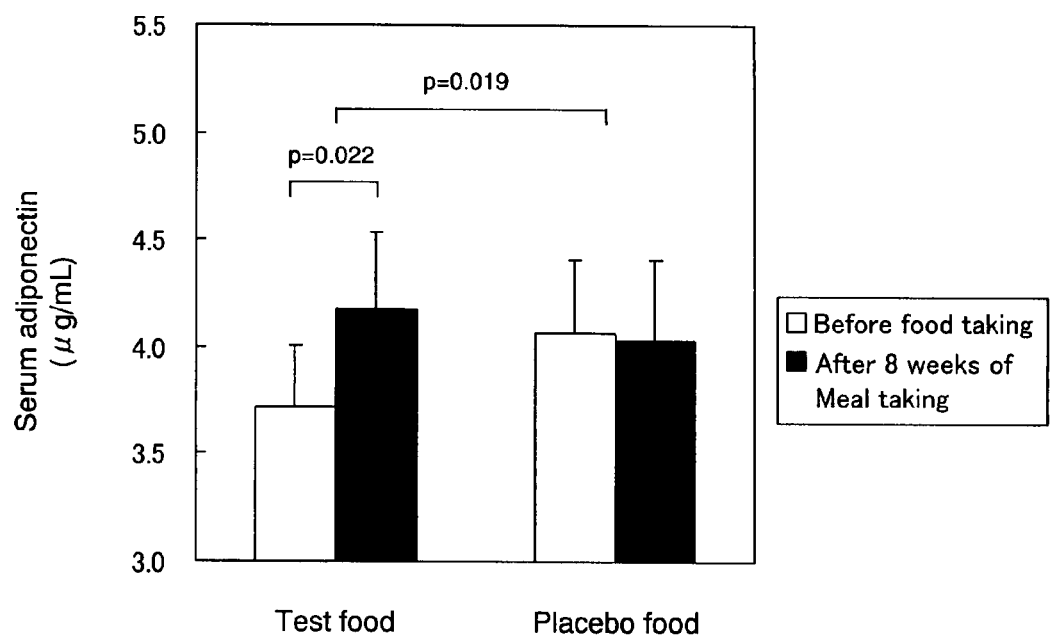
FIG. 4 is a graph showing exemplary results of statistical analysis of data on a concentration of serum adiponectin in human subjects in an example of the present invention.

FIG. 4 and Table 5 below show results of the statistical analysis of data on the concentration of serum adiponectin measured in the above-described blood test. As shown in FIG. 4 and Table 5 below, the test food group exhibited a significant increase in the adiponectin concentration between before the food taking and after eight weeks of the food taking (P<0.05), and there also was a significant difference in the concentration between the test food group and the placebo food group (P<0.05).

TABLE 5

| | Serum adiponectin (µg/mL) | | | |
|---|---|---|---|---|
| | Before food taking | | After 8 weeks of food taking | |
| | Average value | SE | Average value | SE |
| Test food | 3.72 | 0.29 | 4.18 | 0.36 |
| Placebo food | 4.07 | 0.34 | 4.03 | 0.38 |

INDUSTRIAL APPLICABILITY

As described above, the PPAR activator according to the present invention has an excellent PPAR activity, is free from a problem of side effects, can be taken over a long term and can be used preferably for foods or the like. Moreover, nobiletin has an excellent effect of promoting adiponectin secretion. Thus, the PPAR activator according to the present invention can be used as a drug, a supplement, a functional food and a food additive for preventing or relieving diseases such as insulin resistance, hyperinsulinism, type II diabetes, hypertension, hyperlipemia, arteriosclerosis and obesity, etc, for example. It should be noted that this is effective for not only humans but also other animals.

The invention claimed is:

1. A method for activating a peroxisome proliferator-activated receptor (PPAR), comprising:
   administering to a mammal in need thereof an active went consisting of nobiletin in an amount effective to activate the PPAR to treat or relieve at least one disease selected from the group consisting of hyperlipemia and obesity.

2. The method according to claim 1, wherein the nobiletin is derived from a *citrus* fruit.

3. The method according to claim 2, wherein the *citrus* fruit is a Shiikuwasha (*Citrus depressa* HAYATA).

4. A method for treating or relieving at least one disease selected from the group consisting of hyperlipemia and obesity in a mammal, the method comprising administering to the mammal an effective amount of an active agent consisting of nobiletin.

5. The method according to claim 4, which exhibits, in an adipocyte, at least one of a function of inhibiting secretion of TNF-α and free fatty acids and a function of promoting secretion of adiponectin, and which promotes, in a liver cell, β oxidation of fat.

6. The method according to claim 4, which induces at least one selected from the group consisting of apoptosis, differentiation and shrinkage of an adipocyte.

7. The method according to claim 4, wherein the nobiletin is derived from a *citrus* fruit.

8. The method according to claim 4, wherein the *citrus* fruit is a Shiikuwasha (*Citrus depressa* HAYATA).

9. The method according to claim 1, wherein the nobiletin is administered to (1) an adipocyte of the mammal so as to inhibit secretion of TNF-α and free fatty acids or to promote secretion of adiponectin in the adipocyte, or (2) a liver cell of the mammal so as to promote β oxidation of fat in the liver cell.

10. The method according to claim 9, wherein the amount of nobiletin induces PPAR activity in a dose-dependent manner in the adipocyte or liver cell of the mammal.

* * * * *